(12) United States Patent
Jia et al.

(10) Patent No.: US 9,504,424 B2
(45) Date of Patent: Nov. 29, 2016

(54) SKIN SCREW ELECTRODES

(75) Inventors: Wenyan Jia, Wexford, PA (US);
Mingui Sun, Pittsburgh, PA (US);
Robert Joseph Sclabassi, Gibsonia, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 204 days.

(21) Appl. No.: 14/359,904

(22) PCT Filed: Feb. 6, 2012

(86) PCT No.: PCT/US2012/024010
§ 371 (c)(1),
(2), (4) Date: Aug. 26, 2014

(87) PCT Pub. No.: WO2013/077898
PCT Pub. Date: May 30, 2013

(65) Prior Publication Data
US 2015/0126846 A1    May 7, 2015

Related U.S. Application Data

(63) Continuation-in-part of application No. 12/012,607, filed on Feb. 4, 2008, now Pat. No. 8,112,139.

(60) Provisional application No. 61/562,483, filed on Nov. 22, 2011.

(51) Int. Cl.
| | |
|---|---|
| *A61B 5/04* | (2006.01) |
| *A61B 5/00* | (2006.01) |
| *A61N 1/04* | (2006.01) |
| *A61B 5/0478* | (2006.01) |
| *A61B 5/0492* | (2006.01) |

(Continued)

(52) U.S. Cl.
CPC ........... *A61B 5/6839* (2013.01); *A61B 5/0408* (2013.01); *A61B 5/0478* (2013.01);
(Continued)

(58) Field of Classification Search
CPC .. A61B 5/0492; A61B 5/685; A61B 5/6839; A61B 5/04025; A61B 5/04; A61B 5/0531; A61B 5/0533; A61B 5/6824
USPC ......... 600/372–373, 382–384, 386, 390, 393
See application file for complete search history.

(56) References Cited

U.S. PATENT DOCUMENTS

| | | | |
|---|---|---|---|
| 4,270,543 A | 6/1981 | Tabuchi et al. | |
| 4,936,306 A * | 6/1990 | Doty | .................... A61B 5/0484 600/373 |

(Continued)

OTHER PUBLICATIONS

International Search Report and Written Opinion from International Application No. PCT/US2012/24010, dated Jun. 28, 2012, 8 pages.

*Primary Examiner* — Joseph Stoklosa
*Assistant Examiner* — Brian M Antiskay
(74) *Attorney, Agent, or Firm* — Klarquist Sparkman, LLP

(57) ABSTRACT

Electrodes providing excellent recording and physical stability. Electrodes are disclosed that may include a plurality of small teeth that possess a novel design shape and orientation. The shallow and relatively long teeth run parallel to the rim of the electrode that presses against the patient's skin. When the electrode is twisted onto skin, the tiny teeth penetrate the stratum corneum and move nearly horizontally under the stratum corneum, thus anchoring the electrode securely to the skin. The electrodes cause minimal discomfort to the patient since the small teeth do not extend to the pain fibers which are located in deeper layers of the skin. The electrodes may be fabricated in a variety of geometries including cylindrical, disk, and blunt bullet or top shapes. In some instances, the electrodes may be connected to detachable leads having magnetic properties.

29 Claims, 20 Drawing Sheets

(51) Int. Cl.
*A61B 5/0408* (2006.01)
*A61N 1/36* (2006.01)

(52) U.S. Cl.
CPC ........... *A61B5/0492* (2013.01); *A61B 5/6843* (2013.01); *A61N 1/0472* (2013.01); *A61B 5/0006* (2013.01); *A61N 1/0452* (2013.01); *A61N 1/0456* (2013.01); *A61N 1/0464* (2013.01); *A61N 1/0468* (2013.01); *A61N 1/36017* (2013.01)

(56) References Cited

U.S. PATENT DOCUMENTS

| | | | |
|---|---|---|---|
| 5,084,027 A * | 1/1992 | Bernard | A61M 5/3213 206/365 |
| 5,197,471 A * | 3/1993 | Otero | A61B 5/0416 600/386 |
| 5,309,909 A * | 5/1994 | Gadsby | A61B 5/0408 600/386 |
| 5,919,222 A | 7/1999 | Hjelle et al. | |
| 6,091,975 A * | 7/2000 | Daddona | A61B 5/14865 600/309 |
| 6,423,051 B1 * | 7/2002 | Kaplan | A61B 17/3421 604/500 |
| 8,694,080 B2 * | 4/2014 | Farrior | A61B 5/04286 600/508 |
| 2008/0139911 A1 * | 6/2008 | Chandrasekaran | A61B 5/0408 600/382 |
| 2008/0262335 A1 | 10/2008 | Sun et al. | |
| 2009/0024017 A1 | 1/2009 | Ruffini et al. | |

* cited by examiner

SKIN SCREW ELECTRODES

CROSS-REFERENCE TO RELATED APPLICATION

This is the U.S. National Stage of International Application No. PCT/US2012/024010, filed Feb. 6, 2012, which was published in English under PCT Article 21(2) which is a continuation-in-part of U.S. application Ser. No. 12/012,607 (now U.S. Pat. No. 8,112,139), filed Feb. 4, 2008, and also claims the benefit of U.S. Provisional Application 61/562,483, filed Nov. 22, 2011.

BACKGROUND OF THE INVENTION

1. Field of the Invention

The present invention relates to electrodes that are adapted for fast installation and stable implantation into the skin of a subject. The electrodes are useful for a variety of physiological recording and stimulation applications.

2. Description of the Background

The electrical nature of physiological processes has been known for over a century. The electrical components of neuronal activity and the contraction of muscles may be recorded using electrodes placed onto the surface or just below the surface of the skin. Furthermore, excitable tissues, such as nerves and muscles, may be stimulated electrically to achieve various physiological effects.

The electroencephalogram (EEG), as a commonly-utilized diagnostic tool, provides a unique window to observe the functional activity within the brain. Recent technological advances in electronic and computer systems have allowed over one-hundred EEG channels to be recorded simultaneously and modern signal and data processing techniques have provided new insights into the recorded data, both in the temporal and spatial domains. Similar advances have affected the techniques used to record other electrophysiological events in the body, such as electromyograhy (EMG).

Recording of electrophysiological events in the body may be useful in diagnosing a variety of physiological disorders. For example, EEG allows for the non-invasive measurement of the electrical activity of the brain to diagnose epilepsy, sleep disorders, or determine the state of the brain during coma. By assessing the entry of a patient into a sleep state, EEG may also be used to maintain a state of arousal in a patient. EEG in the form of event related potentials (ERPs) is also commonly used in clinical neurophysiology to evaluate the functional or cognitive response of the central nervous system to a certain stimulus. Finally, EEG is currently being employed within systems that establish communication between the brain and an external device—so called brain-computer interfaces.

Despite the recent technological advances and the large number of potential applications, affixing EEG recording electrodes onto the scalp of a subject requires a manual procedure which is a long, difficult process for both the EEG technician as well as the subject. Hair on skin will hinder the ability of the electrode to adhere to the patient. Because of body heat drying the electrolytic gel, the electrode impedance will increase over time. In addition, due to body motion, snagging of the wire leads, and deterioration of the adhesive, electrodes will often disengage. In light of these difficulties, the labor and facility usage costs for electrode installation have been a significant portion of the total cost of clinical EEG studies and have significantly hindered the acceptance of large-array EEG in clinical applications. In addition, some applications require improved electrical access that may be obtained chiefly through the insertion of needle electrodes under the skin. The insertion may be quite painful for the patient and is accompanied by a variety of concerns regarding the safety of the patient.

An additional difficulty encountered during EEG is in the stability of electrode attachment to the body. The electrode is connected to a wire lead which in turn runs to the signal recording device. Because of the natural movements of the patient, the wire leads will often become tangled and pulled by the patient. The electrode will subsequently be pulled off of the skin and require reattachment. The wire leads of common EEG electrodes can also act as tethers which limit the movement of the patient, which in turn limits the potential application of EEG and EMG.

Prior work has attempted to address some of the deficiencies of EEG electrodes. For example, U.S. Pat. Nos. 6,175,753 and 6,201,982 to Menkes et al. discloses quick-placement EEG electrodes. The electrodes disclosed in those patents attempt to avoid the problems associated with hair on the patient by actually attaching the electrode to the hair of the patient, thereby stabilizing the electrode. The electrodes disclosed by Menkes et al. also include a sponge that replenishes the electrolytic gel for prolonged applications. Nevertheless, the electrodes would still suffer from some of the shortcomings of the prior art, including inconsistent electrical contact with the skin due to eventual drying of the electrolyte solutions, physical instability of the electrode, and clinical feasibility of allowing a large number of electrodes to be affixed to the scalp rapidly.

Thus, there has been a long-standing need for electrodes that may be quickly and securely placed on a patient without requiring shaving of the skin or administration of adhesive. In addition, typical electrode administration often employs an abrasion step where a layer of the skin is worn off to improve the signal. Such procedures are time consuming and are often uncomfortable for the patient. The electrodes would preferably be stable after implantation and provide excellent electrical contact to the skin for both recording and stimulation of the tissue in the area of the electrode, with or without the use of electrolytic gels.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated into and constitute a part of the specification, wherein.

SUMMARY OF THE INVENTION

Figure 1:
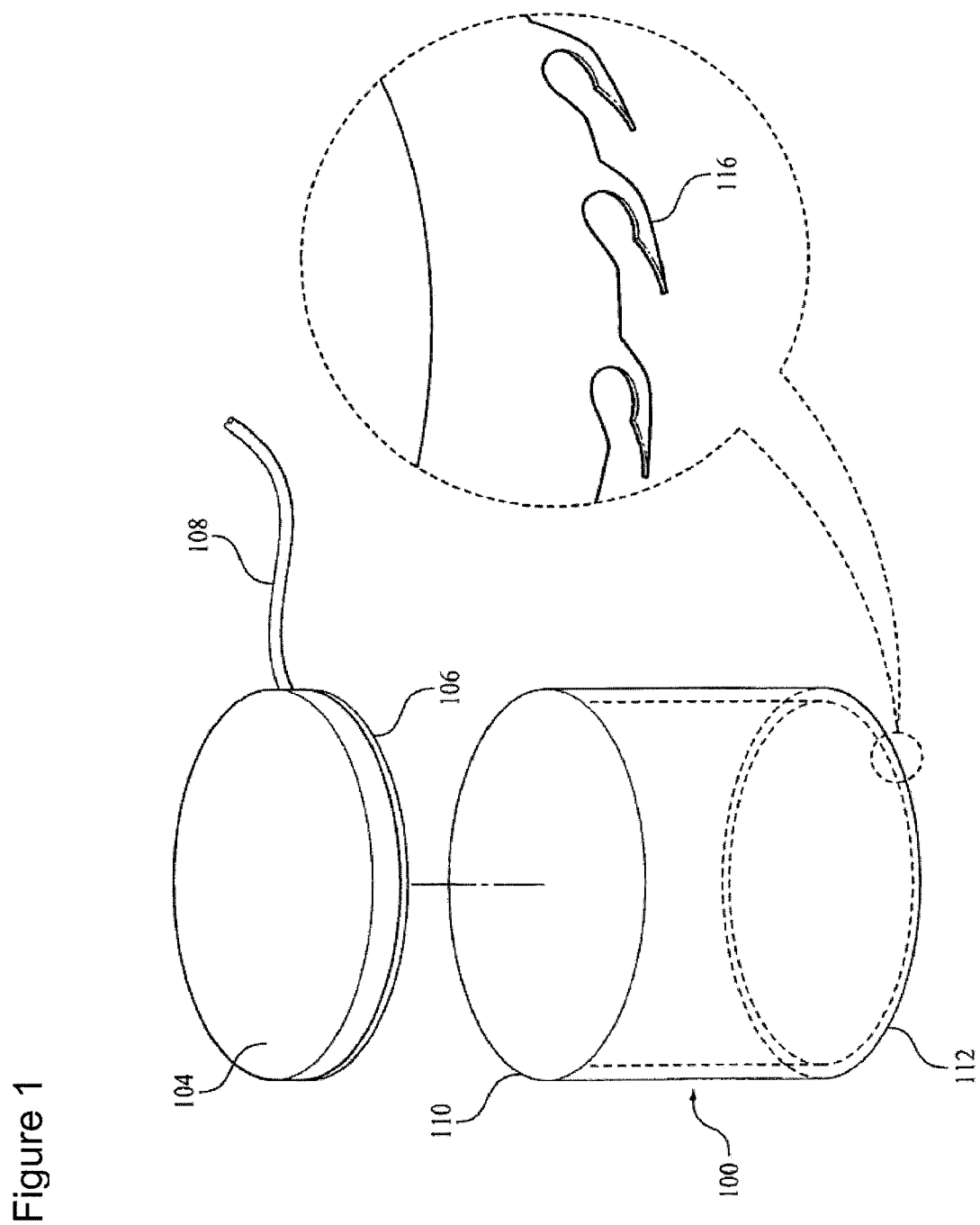
FIG. 1 displays a schematic of an embodiment of the present invention.

The present invention is directed to recording and stimulating electrodes that are easily and stably attached to the skin. The present invention provides a simple, effective, and low-cost design that solves many of the traditional problems associated with the installation of an electrode onto the hairy skin of human and animal patients. The electrodes of the present invention may include small teeth that possess a novel design shape and orientation. The teeth may be fabricated from a hard metal or other material, as well as be coated or electroplated with a conductive metal or other material to promote effective electrical access through the patient's skin. The electrodes of the present invention may optionally include a rubber ring that covers and protects the electrode teeth when the electrode is not in use.

The plurality of shallow and relatively long teeth preferably runs parallel to the rim or surface of the electrode so that they are able to penetrate the patient's skin effectively, but only to a relatively shallow depth. When the electrode is twisted onto skin, the tiny teeth penetrate the stratum corneum and move nearly horizontally with respect to the skin surface under the stratum corneum, thus anchoring the electrode securely to the skin. As such, the electrodes of the present invention preferably do not cause pain because the small teeth do not extend to the pain fibers which are located in a deeper layer of the skin, yet the electrodes provide for excellent electrical access to the interior of the body as well as tremendous physical stability. The electrodes of the present invention may be cylindrical, disc-shaped, or shaped in the form of a blunt bullet or top.

In some embodiments, magnetic leads are used to connect the electrodes electrically with signal processing equipment. The magnetic leads may connect to the cap of the electrodes of the present invention that are fabricated from a metal having magnetic properties. In some embodiments, the cap of the electrode may include a socket where a circular magnetic lead may be inserted to establish electrical connection between the lead and the electrode. The circular magnet lead may be fabricated from a metal or ceramic material. If the material is ceramic, it is preferably coated with a metal, such as gold, to ensure adequate electrical contact between the electrode and the lead.

Because of their superior physical stability, the electrodes of the present invention are well suited to house electronic components that may accomplish a wide variety of tasks. For example, the electrodes of the present invention may include sensors designed to measure blood oxygenation, blood glucose levels, or other common physiological variables. The electrodes the present invention may also be used wirelessly either singularly or as an array so that no electrode leads extend away from the patients body, thereby reducing the annoyance of the electrode assembly for the patient. Implementation of the present invention is particularly appropriate for situations where numerous electrodes are commonly used, such as EEG or EMG recordings.

The electrodes of the present invention may be fabricated either as a single integrated unit or as a multi-component system depending on the specific demands of the application. In certain embodiments, the electrodes of the present invention may be fabricated using precision photo-chemical etching techniques that are well known in the art.

DETAILED DESCRIPTION OF THE INVENTION

It is to be understood that the figures and descriptions of the present invention have been simplified to illustrate elements that are relevant for a clear understanding of the invention, while eliminating, for purposes of clarity, other elements that may be well known. The detailed description will be provided hereinbelow with reference to the attached drawings.

The present invention provides electrodes that may be quickly and stably attached to a patient's skin. The electrodes of the present invention do not require any pre-treatment of the skin to be applied and as such represent a significant improvement over the prior art. In addition, the electrodes of the present invention may be applied to hairy skin (e.g., scalp) of a patient. Insofar as the present invention has general applicability, as used herein, "patient" refers to both human and animal subjects who either have a medical condition or are healthy. The electrodes of the present invention provide superior physical stability and electrical access to the skin of the patient, thus representing a significant improvement over the prior art. The electrodes of the present invention may be employed both as stimulating electrodes and recording electrodes as detailed hereinbelow.

The electrodes may possess a variety of shapes and geometrical configuration of the teeth. The general structure of an electrode 100 of the present invention is shown in FIG. 1. The electrode 100 is generally cylindrical in shape with a hollow interior that is capable of housing electronic components as described further hereinbelow. The electrodes 100 may include a magnetic cap 104 attached to a brass plate 106 from which an electrical lead 108 may extend. The magnetic cap 104 may attach to the distal rim 110 (i.e., the portion of the electrode that is away from the skin of the patient) of the electrode, thus forming the outside portion of the chamber within the body of the electrode. The electrodes 100 preferably have a diameter of about 10 millimeter for easy handling; however, the diameter may vary considerably depending on specific applications. The proximal rim 112 of the electrode (i.e., the portion of the electrode that rests against the skin of the patient) includes a plurality of teeth 116 (shown at higher resolution in FIG. 2) that extend therefrom.

Figure 2:
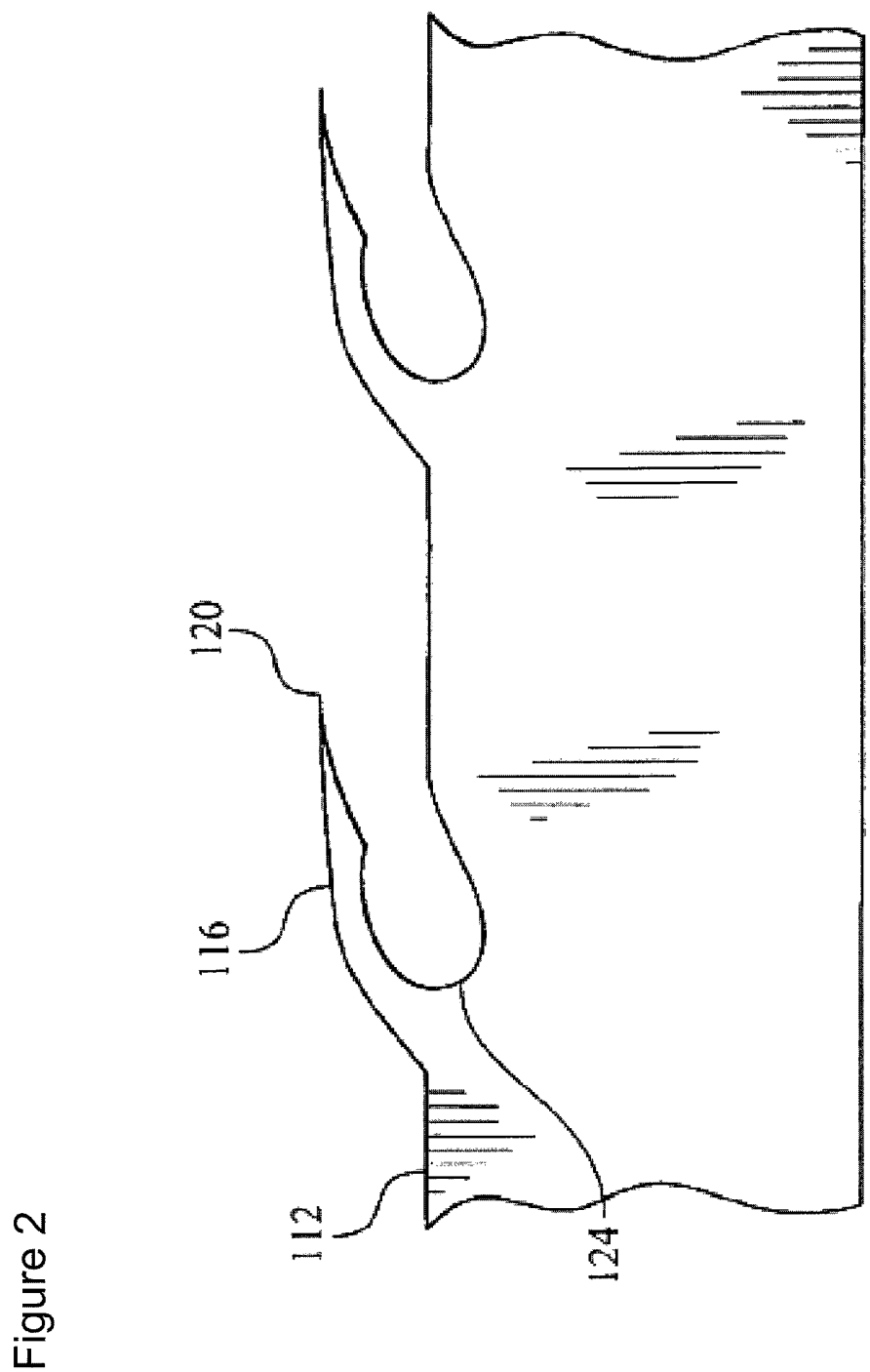
FIG. 2 is a close-up view of the teeth of the electrodes of the present invention.

A higher resolution of the proximal rim of the electrodes of the present invention is shown in FIG. 2. In the cylindrical electrode embodiments, the teeth 116 may run parallel to the proximal rim of the electrode though the specific geometry of the teeth may vary widely. The teeth 116 may extend between 0.002 inches and 0.005 inches from the proximal rim 112 of the electrode. The teeth 116 may be oriented from about 2° to about 5° away from the rim 112. The teeth 116 preferably have a sharp tip that allows for easy penetration of the epidermis. The length of the teeth 116 may vary widely depending on the particular implementation, with presently preferred embodiments having a length of about 0.005 inches to about 0.05 inches with a length of about 0.01 inches being presently preferred.

As seen in FIG. 2, at the base of the teeth 116 a small recessed area 124 may be present. This recessed area 124 is well suited to capture any hair that may be present on the surface of the patient's skin. A wide variety of shapes for the recessed area 124 may be used depending on the particular application where the electrodes are employed. By employing this configuration, the electrodes 100 of the present invention are secured to the surface of the skin regardless of the presence of the hair. The electrodes 100 of the present invention thus avoid any need for manually paring the hair or shaving the patient prior to placement.

The teeth 116 may be of a length and angle such that they are capable of penetrating the epidermis to just past the level of the stratum corneum. The specific length, shape, and angle of the teeth 116 of the electrodes of the present invention may be varied widely, with embodiments where the teeth 116 penetrate the epidermis past the stratum corneum, though preferably not to the level of pain fibers. Orientation at such a slight angle from the surface of the electrode limits the penetration depth of the teeth 116 of the present invention is limited, thereby drastically reducing discomfort for the patient. Additionally, the plurality of teeth 116 forms a sturdy attachment to the skin through the interaction with the stratum corneum. When piercing the skin (particularly the scalp), the electrodes of the present invention should be applied quickly to minimize the discomfort to the patient.

By piercing the stratum corneum and reaching the water-containing portions of the epidermis below, the electrodes of the present invention also provide excellent electrical access to the patient with electrode impedance on the order of 5 kΩ being commonly observed without use of any electrolytic gels. The electrodes of the present invention may also be used with electrolytic gels to improve impedance as the particular situation warrants. In those instances where an electrolytic gel is used, the electrodes of the present invention may be pressed and turned lightly into a sheet of hydrogel that contains an amount of ionic electrolyte compound The shape, size, and material properties of the teeth may be varied in the design of the electrodes of present invention. Since the teeth are typically very small, the material from which the teeth are fabricated is preferably be both sufficiently hard and stress resistant so that the teeth will not bend or break off during electrode installation. Stainless steel alloy may be effectively employed in fabricating the electrodes of the present invention in that it achieves an appropriate hardness after annealing. In certain embodiments, the steel alloy includes a sufficient amount of iron to achieve magnetic permissibility for lead wire connection as described below. In other embodiments, the teeth may be coated or electrochemically plated with a conductive metal (e.g., gold or silver) to improve the electrical properties of the electrodes.

In order to improve performance, the electrode teeth may be coated or electroplated with a material of low half-cell potential (e.g., silver-silver chloride), an anti-oxidation metal (e.g., gold), or a high electron-transfer material (e.g., iridium). The electrodes may be fabricated as a single unit made entirely from one type of material. In other embodiments described below, the body of the electrode may be made of multiple components including plastic or other non-conductive materials. In some embodiments, the teeth of the electrode may include a nickel-containing alloy (e.g., stainless steel). To reduce the likelihood or severity of reactions in patients who are allergic to nickel, the teeth of the electrodes of the present invention may be coated with a metal or conductive metal oxide. The electrodes of the present invention may be synthesized from a material that is either disposable or autoclavable, thus eliminating cross-infection potential in human applications.

In some embodiments of the present invention, the electrodes possess the approximate external dimensions of prior art EEG electrodes (on the order of 1 centimeter). However, alternative dimensions that are tailored to the specific application may also be employed. For example, if electrodes are to be used on a small patch of skin, a small animal, or applied using an automatic tool, the diameter of the electrode could be reduced.

Figure 3:
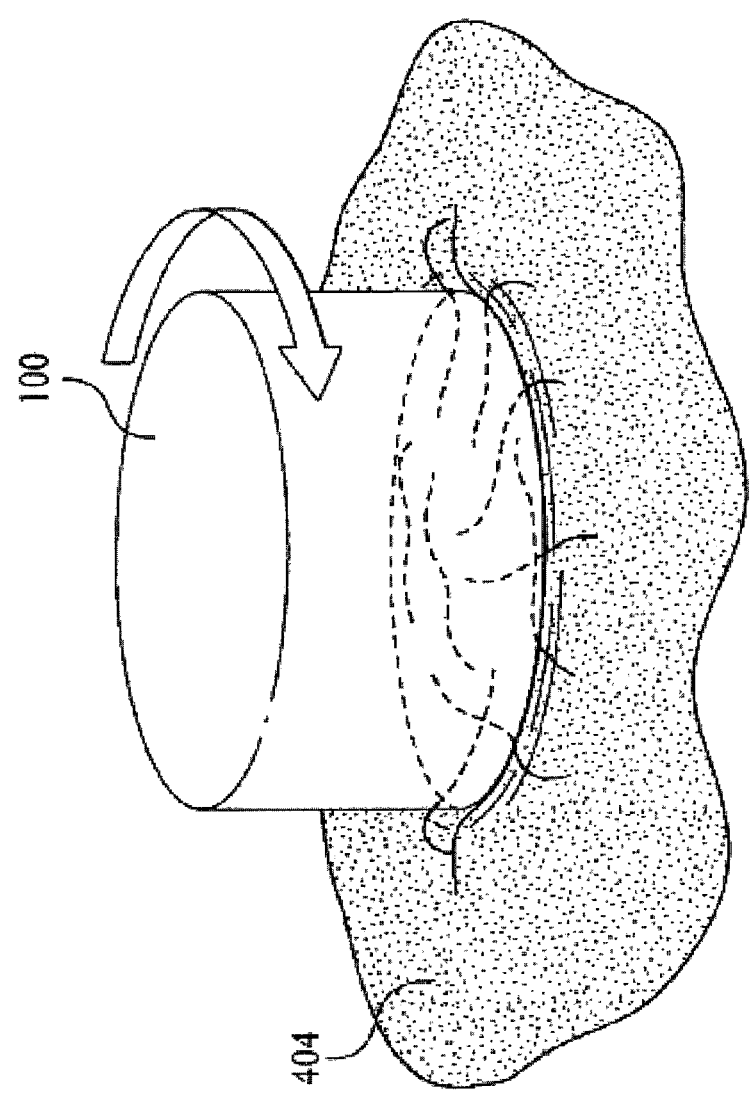
FIG. 3 depicts how an embodiment of the present invention may be attached to the body of a patient.

The application of the electrode to a patient's skin may be made by slightly pressing towards the body while turning the electrode 100 clockwise as shown in FIG. 3. Accordingly, the electrode 100 is thus quickly and firmly affixed to the patient's skin 404. The application of the electrode typically causes no pain since the depth of penetration is not sufficient to reach the pain receptors located in the deeper portions of the skin. After the electrode is applied to the patient, all of the teeth may extend nearly horizontally under the stratum corneum resulting in a large total electrical contact area and a secure attachment to the skin.

In many prior art electrodes, the electrode lead is permanently connected to the electrode. As the number of electrodes installed on the scalp, for example, increases, the space above the head becomes cluttered with wires. In addition, when an electrode lead is accidentally pulled, the electrodes may separate from the scalp requiring a complete re-installation. The present invention overcomes these limitations. In certain embodiments, a magnetic disk glued to a brass plate makes electrical contact between the wire lead (which may be soldered to the brass plate) and the electrode as shown in FIG. 1. As such, in the present design magnetic attraction may be used to connect electrodes to the wire leads. This innovation provides a number of advantages: 1) electrodes can be easily separated from the leads, making their use convenient for the patient (e.g., for taking a shower or leaving the recording room temporarily); 2) it further facilitates the use of a hand-held installation devices, as described below; and 3) when any electrode lead is accidentally pulled, only the magnetically connected lead will separate, while the electrode placement on the patient's skin will not be disturbed. In other embodiments, the electrode may be fabricated from materials that are not magnetic. In those embodiments, the wire lead may be reversibly attached to the electrode in a variety of manners, such as adhesive, snap joints, or other methods commonly known in the art.

Figure 4:
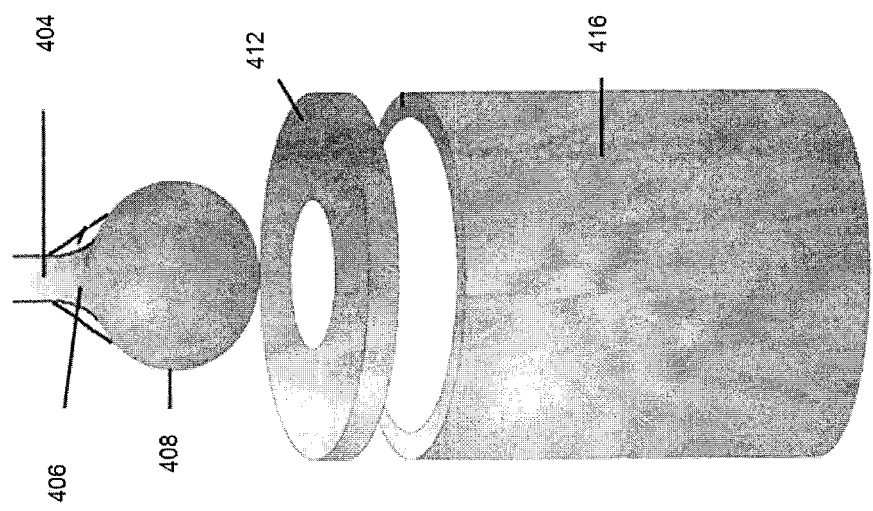
FIG. 4 shows an electrode of the present invention having a magnetic lead.
Figure 5:
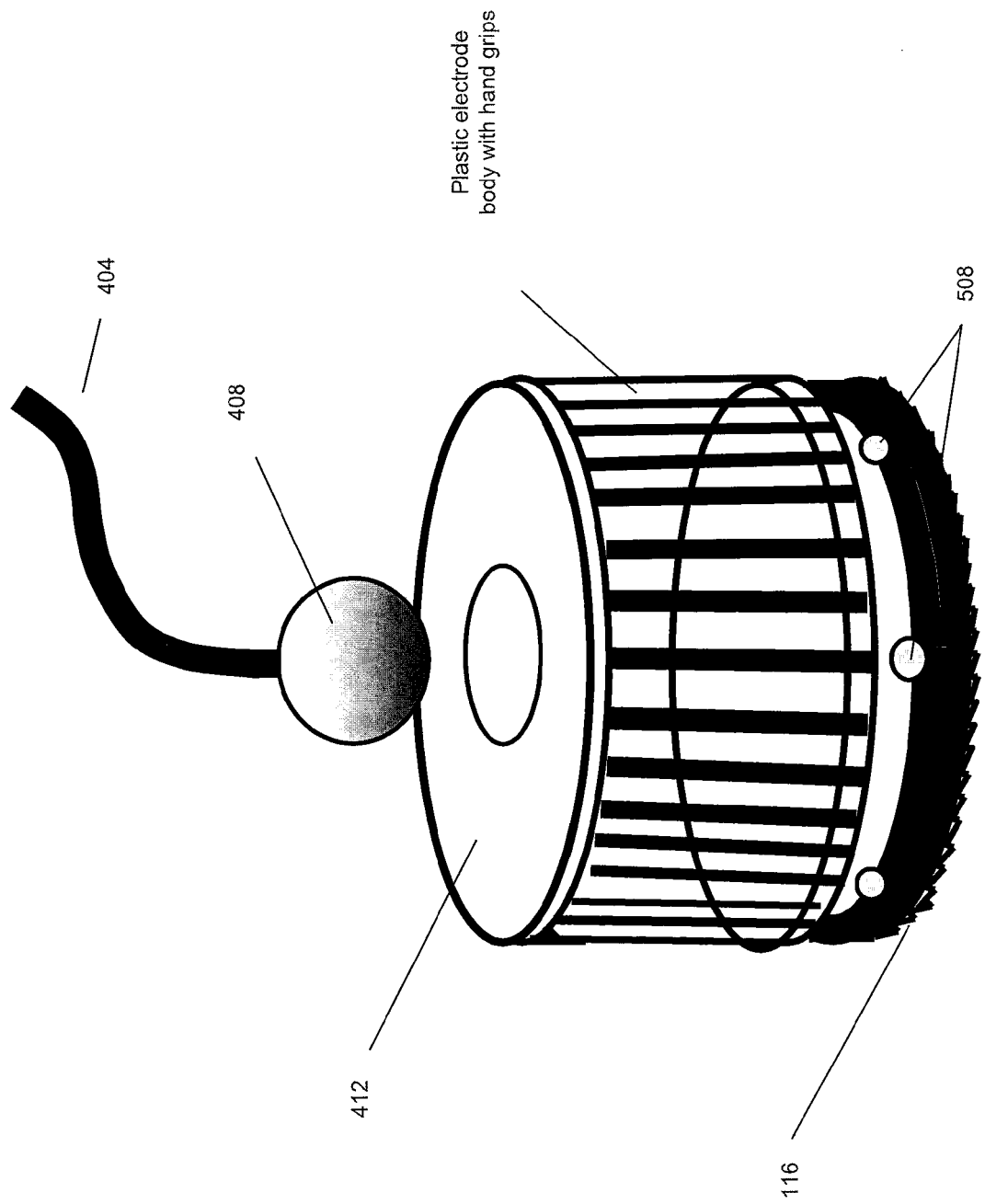
FIG. 5 shows another electrode of the present invention having a magnetic lead and a plastic electrode body.

The electrodes of the present invention may also implement a magnetic lead 400 in a different manner. The wire lead 404 may be soldered 406 to a magnetic sphere 408 as shown in FIG. 4. The magnetic sphere 408 may fit into the hole of a paramagnetic cylindrical disk 412 having a hole in its face (e.g., a steel washer) that is able to be attached or joined to an electrode body 416. The cylindrical disk 412 may also be fabricated from any other material that possesses magnetic properties. To improve the electrical connectivity between the magnetic sphere and the washer, the sphere 400 and/or washer 412 may be plated or coated in whole or in part with an electrically conductive material such as gold. The body of the electrode 504 may also be fabricated from plastic as shown in FIG. 5 to provide a lighter-weight electrode. The plastic body 504 may include metal components that create connectivity between the teeth that are placed in the patient and the conductive cap 412. The plastic body 504 may be attached to the teeth 116 by heat activated locks 508 or any other securing mechanism.

Figures 6A, 6B:
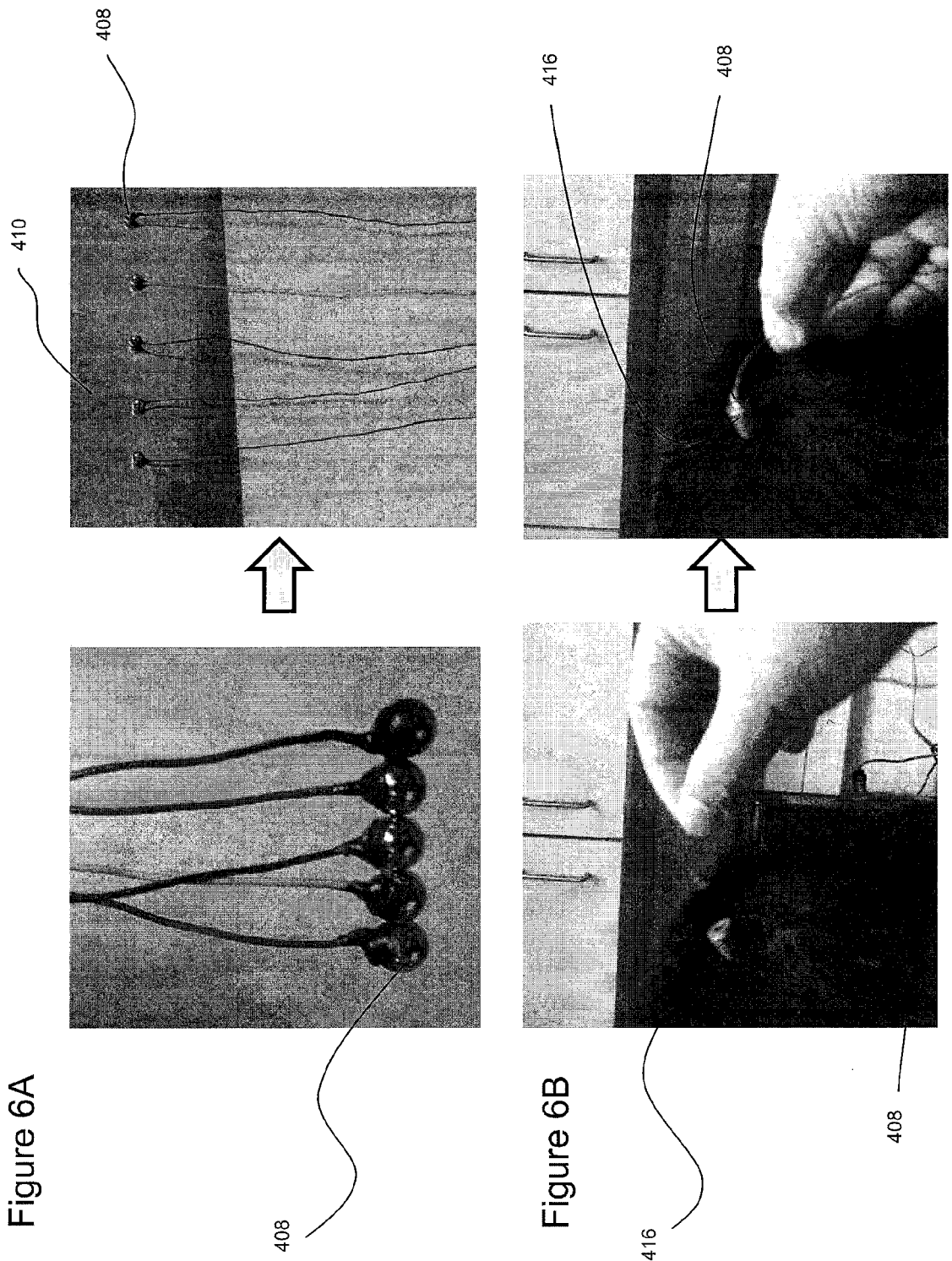
FIG. 6A displays the magnetic leads of the present invention.
FIG. 6B displays the use of a magnetic lead with an electrode of the present invention.

The magnetic leads provide for improved ease of use both in storage and application. FIG. 6A shows how magnetic leads 408 may be easily stored in a group due to their magnetism or on a metal strip 410 near the patient. That property allows the leads 408 to be selected individually and attached easily to the electrode body 416 as shown in FIG. 6B.

Figure 7:
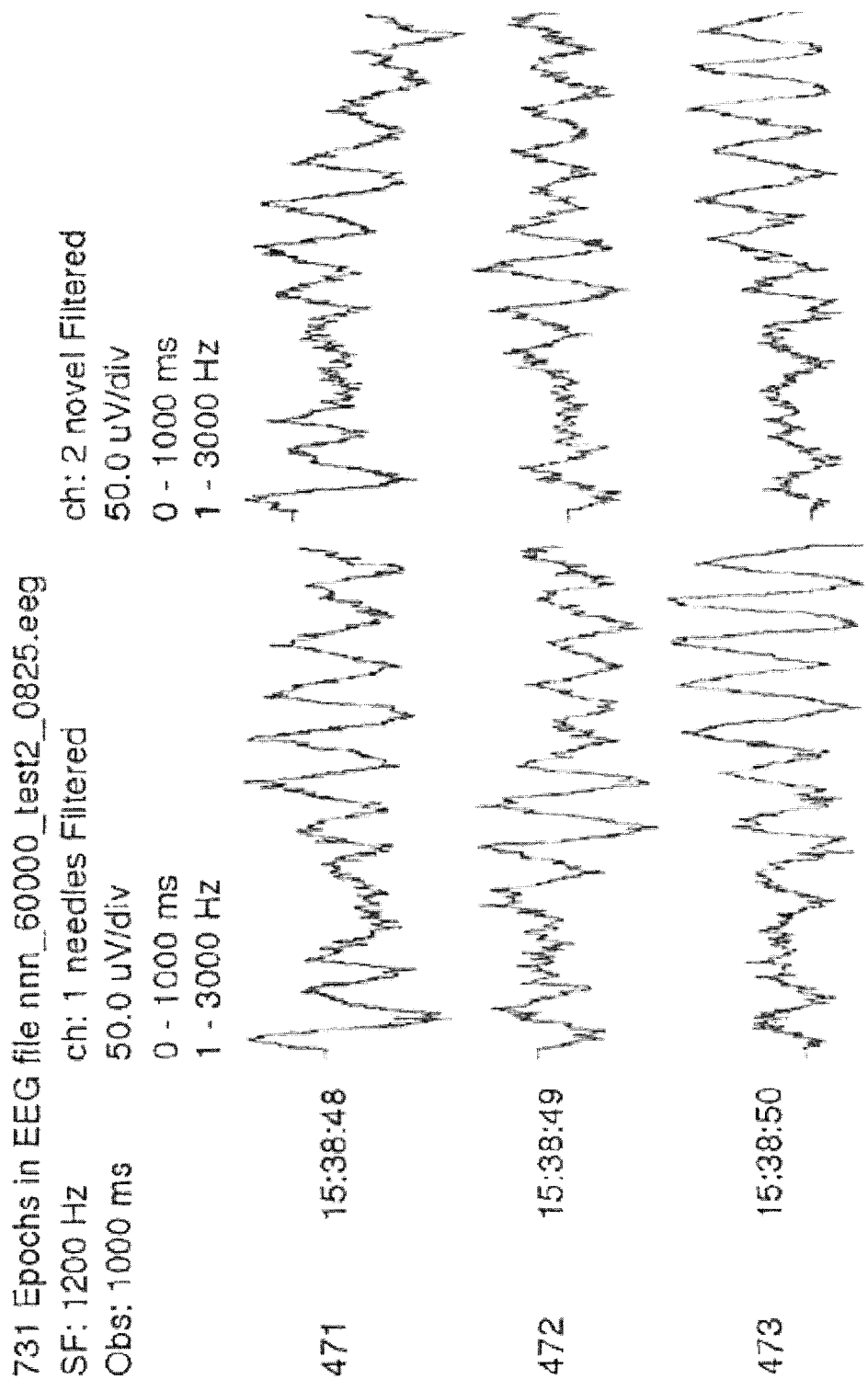
FIG. 7 depicts an EEG recorded with cylindrical electrodes of the present invention.
Figure 8:
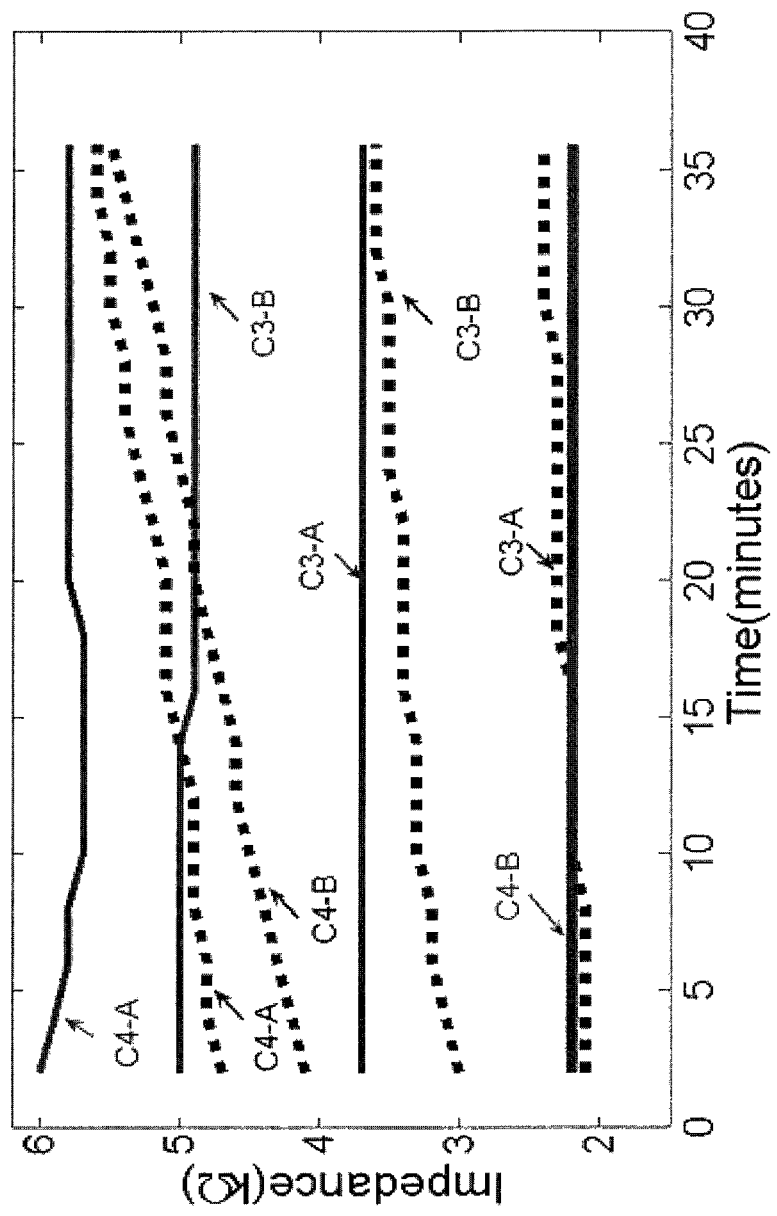
FIG. 8 displays the impedance variation over time with electrodes of the present invention.

FIGS. 7 and 8 display physiological data collected from patients. FIG. 7 shows EEG data collected from a patient using electrodes of the present invention. FIG. 8 demonstrates that the impedance using the electrodes of the present invention is relatively stable after placement and improved compared to standard prior art skin electrodes. Electrodes were placed at two scalp sites (C3, C4) on two separate patients (A, B) using both prior art disk electrodes (solid lines) and skin screw electrodes of the present invention (dashed lines). The skin screw electrodes of the present invention maintained consistent electrical contact during the entire experiment as shown.

Figure 9:
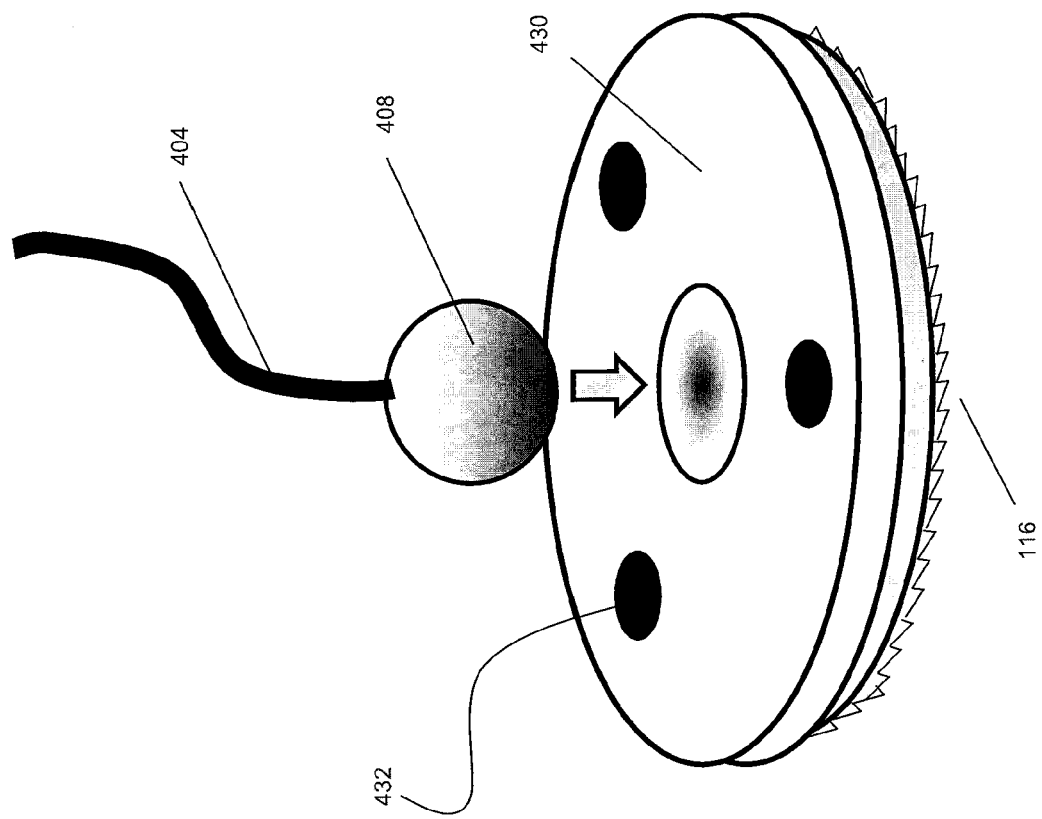
FIG. 9 presents another embodiment of an electrode of the present invention.

Another embodiment of the electrodes of the present invention is shown in FIG. 9. In some embodiments, the electrode body 430 may have a low disk-like profile. This allows the patient to wear the electrode more comfortably while sleeping or during normal daily activities and would further reduce risks of displacement associated with inadvertent bumping of the electrode. The disk-like electrode 432 may be fabricated having a spherical socket or hole into which a magnetic sphere 408 connected to a wire lead 404 may be placed. The disk-like electrode embodiment 430 may also include holes 432 into which an applicator apparatus may be inserted. Thus, the practitioner who applies the electrodes would be able to twist the electrode into place even with a low profile of the electrode body. In this and other electrode embodiments, the novel teeth of the present electrode may be present not only at the rim of the electrode but also in additional geometric patterns across the face of the electrode. The teeth may be present in concentric circles, rows, or any other configuration useful for the particular application. When implemented as concentric circles, the multiple concentric sets of electrode teeth may be electrically independent of one another and act as independent electrodes for multiple implementations including the localized measurement of voltage in a patient.

Figure 10:
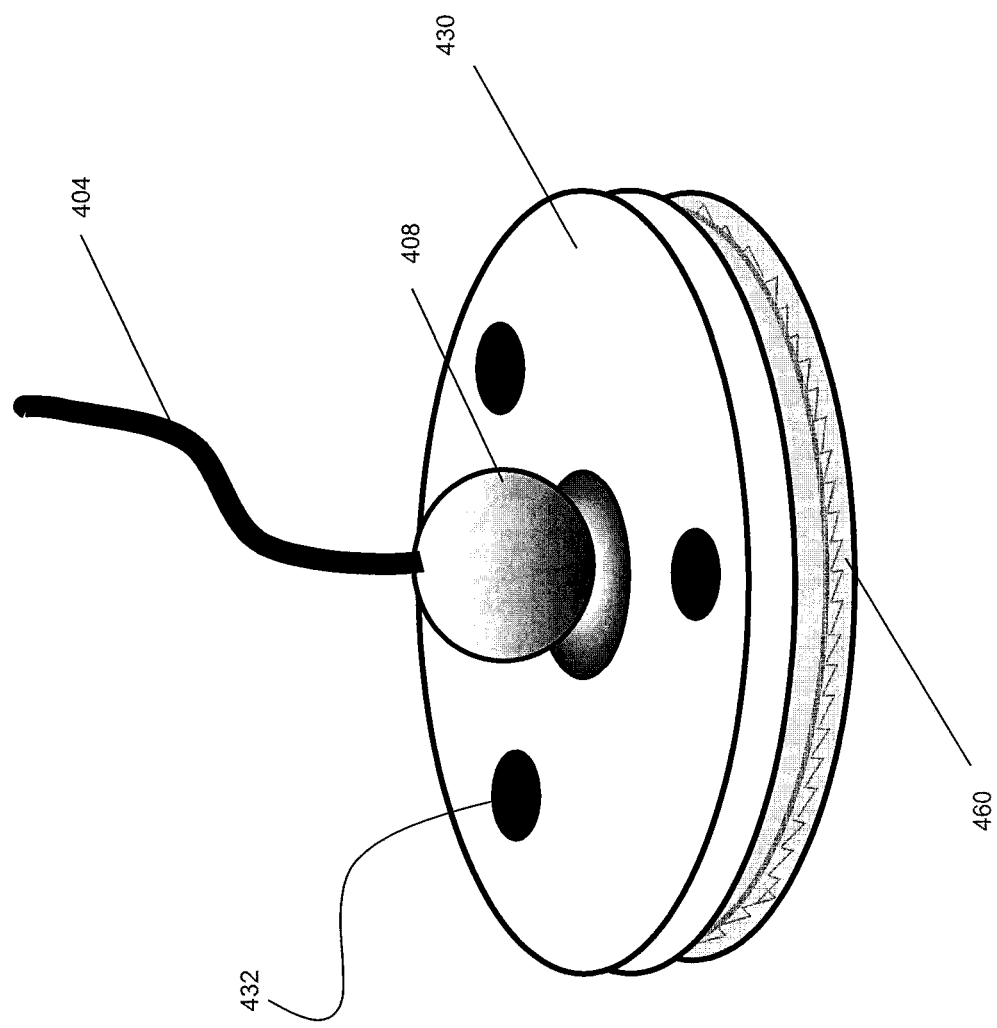
FIG. 10 depicts an embodiment of an electrode of the present invention that includes a rubber ring that covers the teeth of the electrodes of the present invention.
Figure 11:
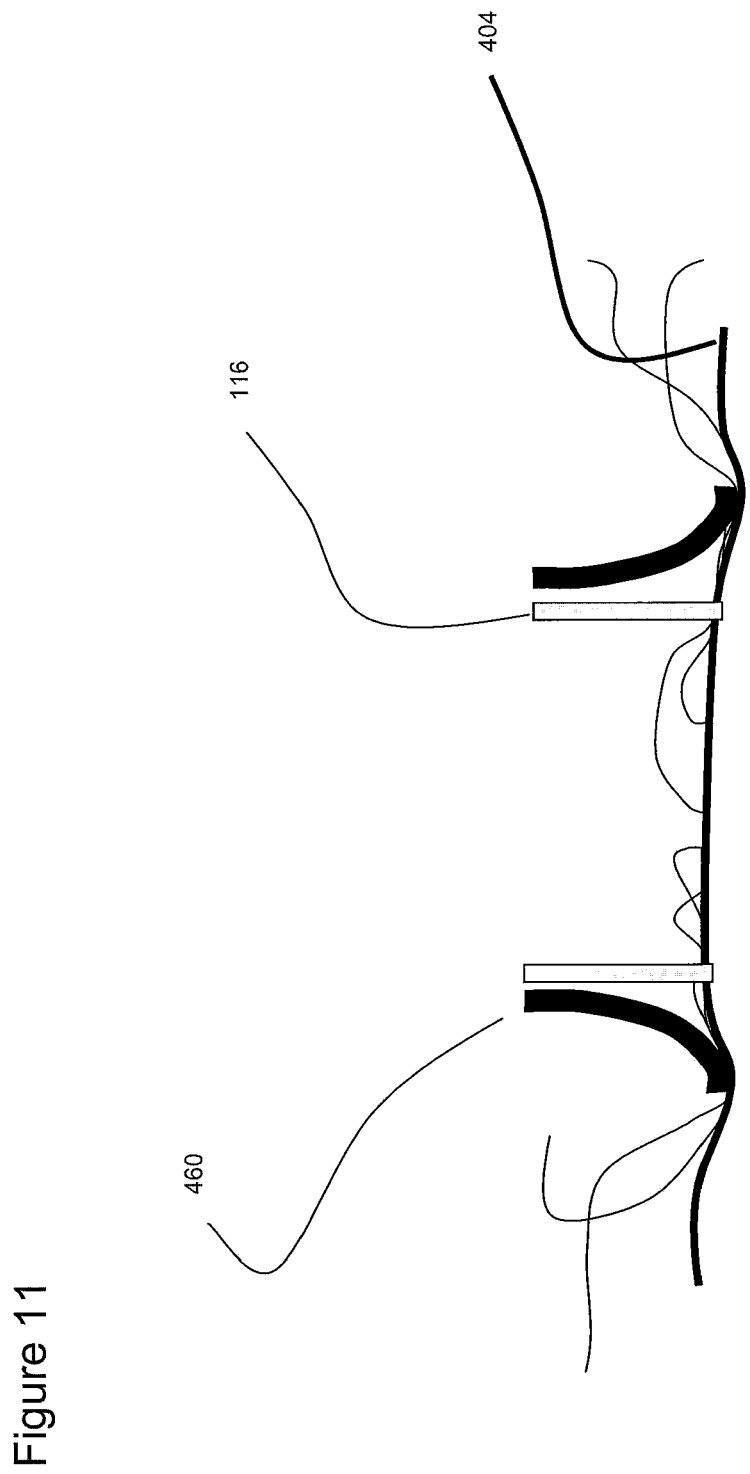
FIG. 11 is a schematic of how the rubber ring may interact with the skin of a patient.

The electrodes of the present invention may also include a rubber ring 460 that surrounds the base of the electrode as shown for a disk-like electrode body in FIG. 10. While shown for a disk-like electrode body, the rubber ring 460 may be used in all of the geometric configurations of the electrodes disclosed herein. The rubber ring 460 would both protect the teeth 116 of the electrodes from inadvertent bending prior to use and also be useful for moving hair away from the site of electrode application as shown in FIG. 11.

Figure 12:
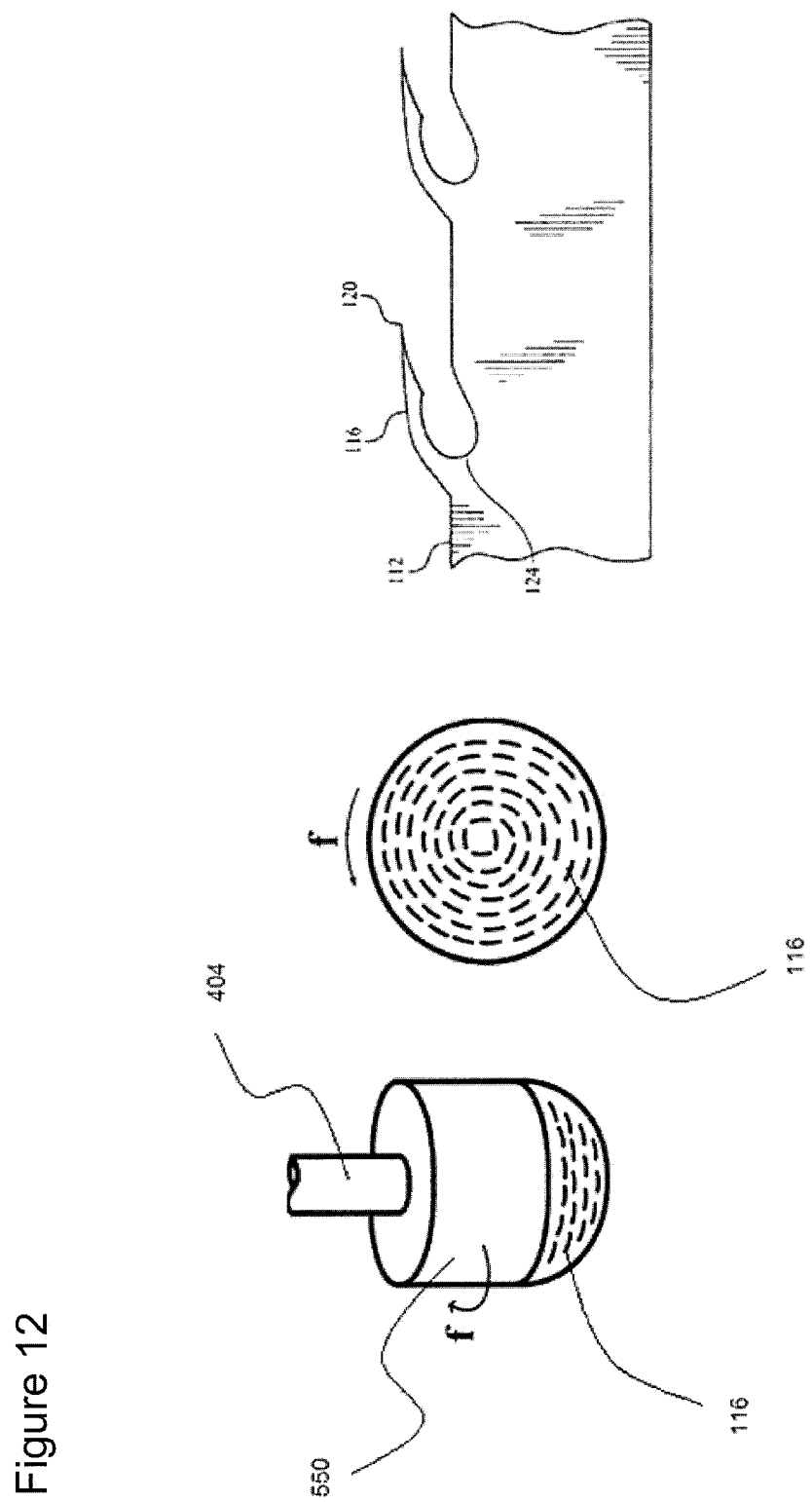
FIG. 12 presents another embodiment of an electrode of the present invention.
Figure 13:
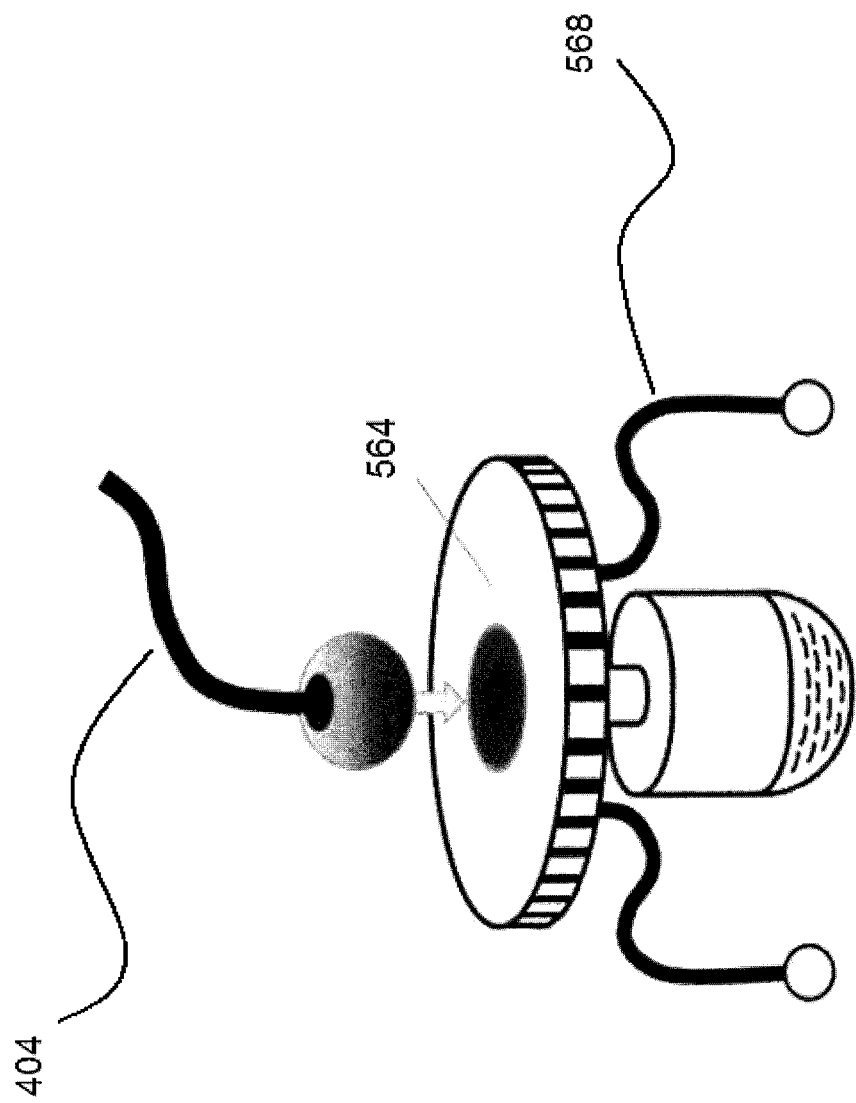
FIG. 13 presents another embodiment of an electrode of the present invention.

An additional embodiment of the electrodes of the present invention is shown in FIG. 12. In this embodiment, the electrode body 550 is shaped like a blunt bullet or a top. The electrode teeth 116 may be located across the bottom face of the electrode 550 and allow the electrode 550 to be attached to the patient across many angles. This embodiment of the electrodes of the present invention is shown in FIG. 12 with an integrated wire lead 404. This embodiment is particularly helpful for electrode placement in curved body areas. The "blunt bullet" embodiment also is able to penetrate hair easily to provide a strong electrical and physical connection to patient's skin. This embodiment may also be implemented in a configuration having a twisting knob 564 at the top for ease of attachment to patients. The twisting knob 564 may be magnetic so as to be compatible with the use of the magnetic leads 404 as described hereinabove. This electrode may include stabilizing legs 568 that rest on the skin of the patient and provide additional support for the electrode once it is attached as shown in FIG. 13.

Figure 14:
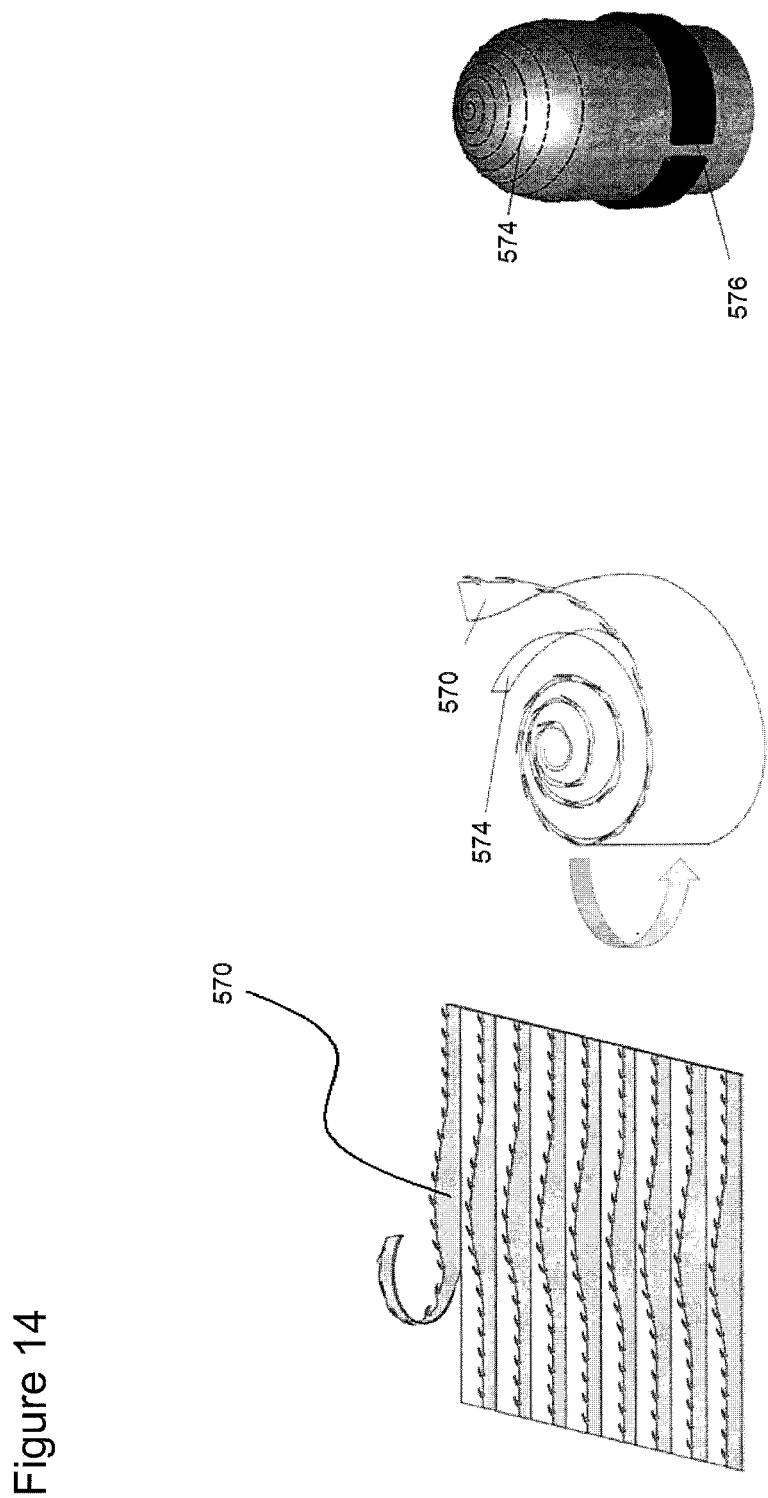
FIG. 14 shows a method by which the electrode displayed in FIG. 12 may be fabricated.

The "blunt bullet" type electrodes may be formed using a single strip of metal. For example, a strip of metal 570 that includes the electrode teeth may be fabricated using the commonly known technique of photochemical etching (or photochemical milling). After a protection film is formed on desired portions of the sheet, a series of chemical etching will be utilized to form the microscopic teeth of all electrodes simultaneously. Next, each strip 570 will be peeled from the sheet and rolled precisely together with a spacer sheet 574 (which has the same shape but no teeth), as shown in FIG. 14. The strip of metal preferably has a profile which, when rolled into a coil, will provide the desired profile for an electrode body. For example, in some embodiments, the metal strip may be widest on one side and decrease in width across the length of the strip. When rolled into a coil, that embodiment will display a profile of a blunt bullet type electrode body 576. The layers of the roll may thus be arranged appropriately so that the blunt bullet shape of the electrode tip and the swirl pattern of the teeth will be both formed. The rolled sheets may then be fixed or fused in place using adhesive, soldering, epoxy, or other fixation mechanism, such as a clamping ring 576 as shown in FIG. 14. After rolling, the teeth will preferably be distributed uniformly across the electrode surface, though any distribution of teeth may be obtained by designing the etching appropriately. An alternative approach to fusing the rolled sheets into place is to pre-coat the sheet with a layer of sintering agent and heat-treat the completed rolls using a standard vacuum sintering process. The resulting electrode has a surface with the novel teeth of the present invention in a swirl or spiral pattern across its face. While shown in FIG. 14 for a blunt bullet shape electrodes, the same process may be used to fabricate any geometric configuration of electrode.

Figure 15:
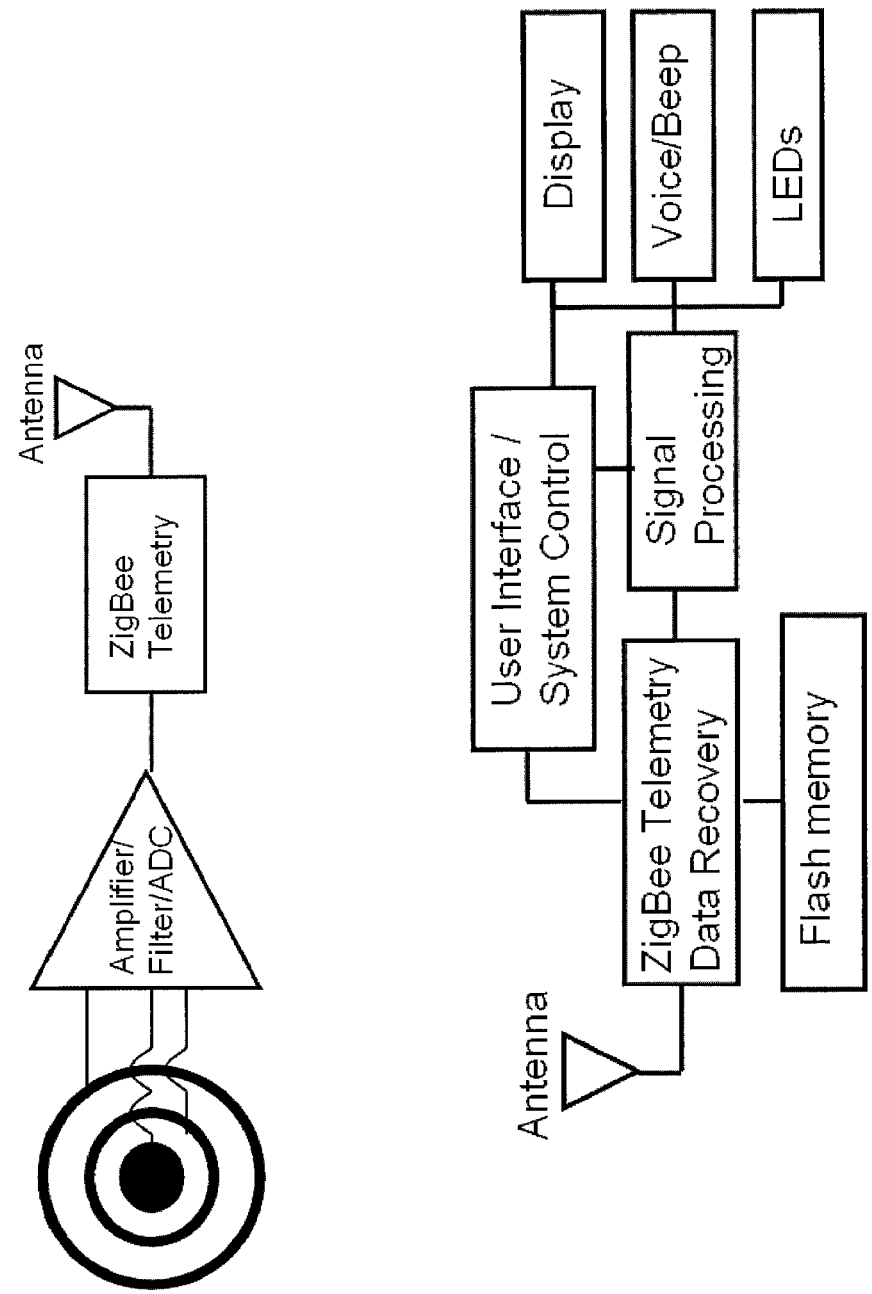
FIG. 15 depicts a schematic of the electronics that may be used with the electrodes of the present invention.

Since the electrode design of the present invention provides an electrically-shielded space inside the electrode, electronic circuits may be placed within this space, converting the passive electrode into an active device. The signal may be amplified through an amplifier within the interior of the electrode where the outer rim is grounded, thus providing an ideal shield from exterior interference. The interior space may also contain a small battery and a telemetric circuit (e.g., RF, infrared, or BLUETOOTH), providing power and transmitting a single channel to a nearby receiver (e.g., a cell phone, PDA, other hand-held electronic device, or receiver attached to a recording device). An example of the circuitry that made be used with the electrodes of the present invention is shown in FIG. 15. The electrodes may be used in either a wired configuration having wire leads or wirelessly for the high fidelity collection and transmission of data.

While the implementation of the present invention shown in FIG. 15 is for recording an electrical signal, the electrodes of the present invention, when equipped with the appropriate electronic components, may also act as stimulating electrodes. As a stimulating electrode, the present invention could be used in a wide variety of situations to deliver small currents to underlying tissues. For example, prior art techniques such as transcutaneous electrical nerve stimulation (TENS) and percutaneous electrical nerve stimulation (PENS) have been used to treat chronic pain that is not responsive to other treatments. The electrodes of the present invention provide a tremendous tool for use in these applications and may be modified for use in those areas by the inclusion of well-known electronic components and circuitry.

Figure 16A:
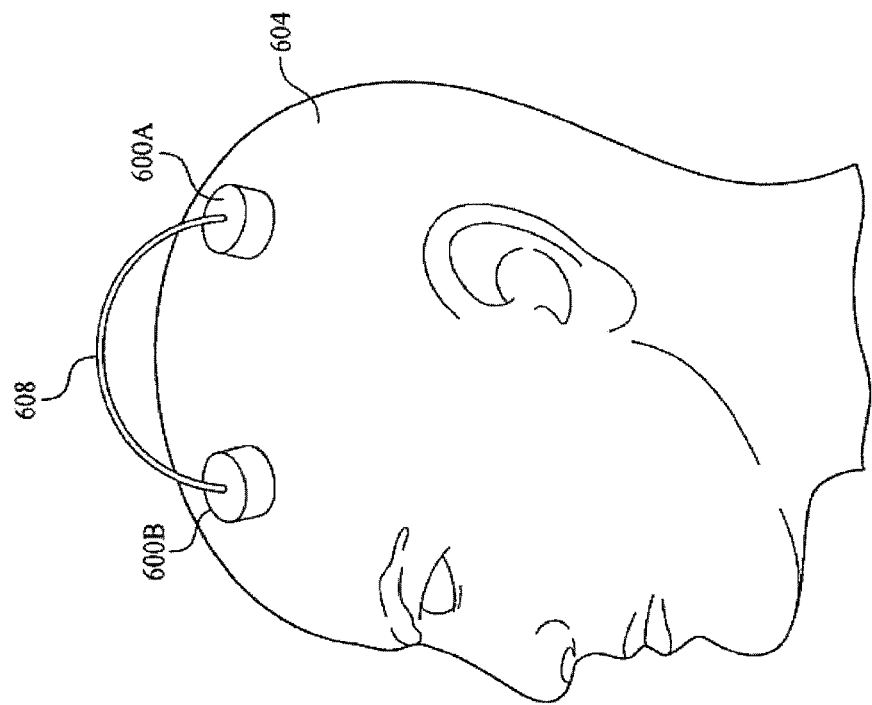
FIG. 16A-D shows multiple configurations of electrodes of the present invention that may be used in recording from a patient.

The electrodes of the present invention may also be used in arrays of two or more to create ultra-portable, wireless recording devices capable of high fidelity collection and transmission of data. As shown in FIG. 16A, two electrodes 600A, 600B may be applied to the scalp of a patient 604 with a cable 608 connecting the two electrodes 600A, 600B. In that configuration, the cable 608 may communicate data and power between electrodes 600A, 600B while at the same time acting as an RF antenna. In certain embodiments, the cable 608 may be shielded, with the shield acting as the antenna for data transmission and reception. The antenna could be used to transmit the amplified EEG signal to a nearby computer or receiving station using any standard protocol such as BLUETOOTH.

Figure 16C:
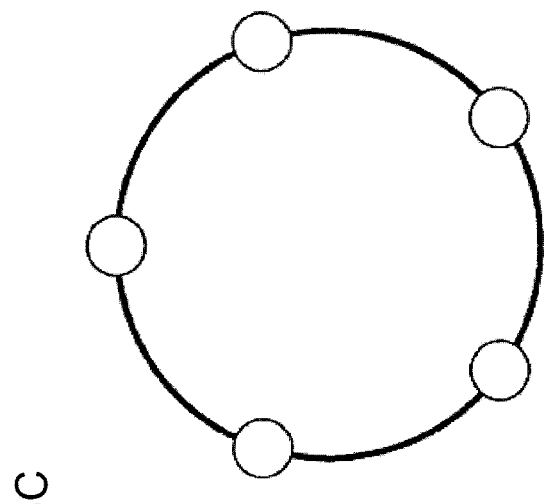
Figure 16B:
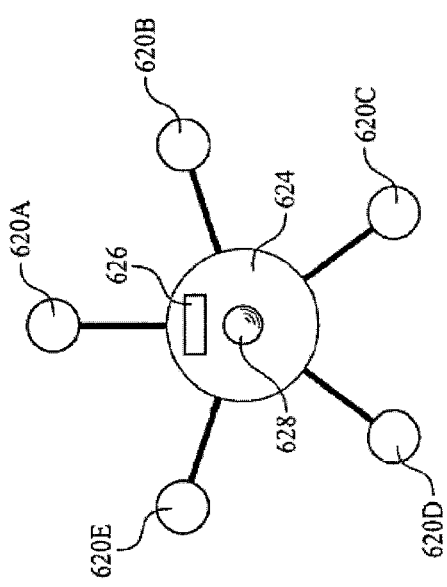
Figure 16D:
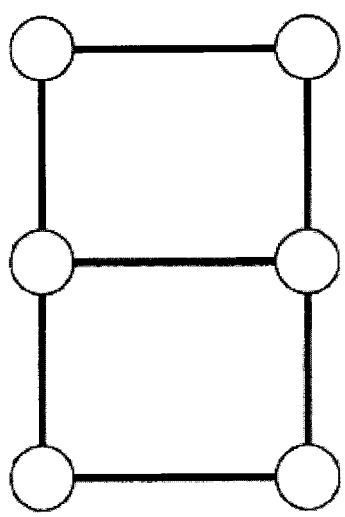

In other configurations, electrodes 620 could be placed in a star pattern (FIG. 16B) with a central unit 624 that may connect to the patient using the same small teeth as the electrodes 620. The central unit 624 can be either an electrode or a non-electrode, including electronic components such as a switch to turn on or off the device or a gain control 626. The central unit 624 may also include an infrared light emitter 628 for the telemetric transmission of data. Multiple electrodes may also be placed in a loop (FIG. 16C) or a net (FIG. 16D) configuration. By using multiple electrodes, the number of channels of data that are recorded simultaneously may be increased. One of skill in the art will recognize a wide variety of configurations that may be employed depending on the physiological data that is to be collected (e.g., EEG, EMG, or EKG).

Figure 17:
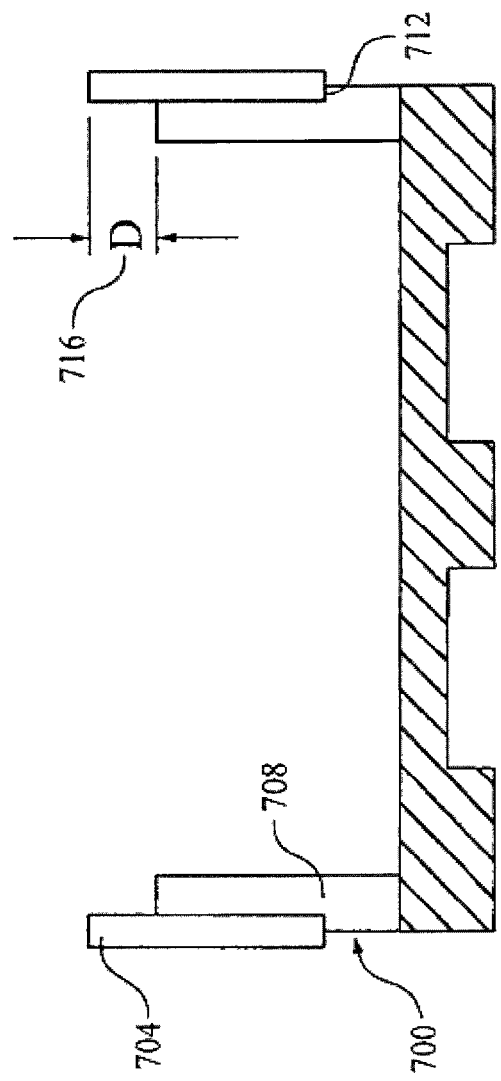
FIG. 17 depicts a cut-away view of a multi-component electrode design of the present invention.
Figure 18:
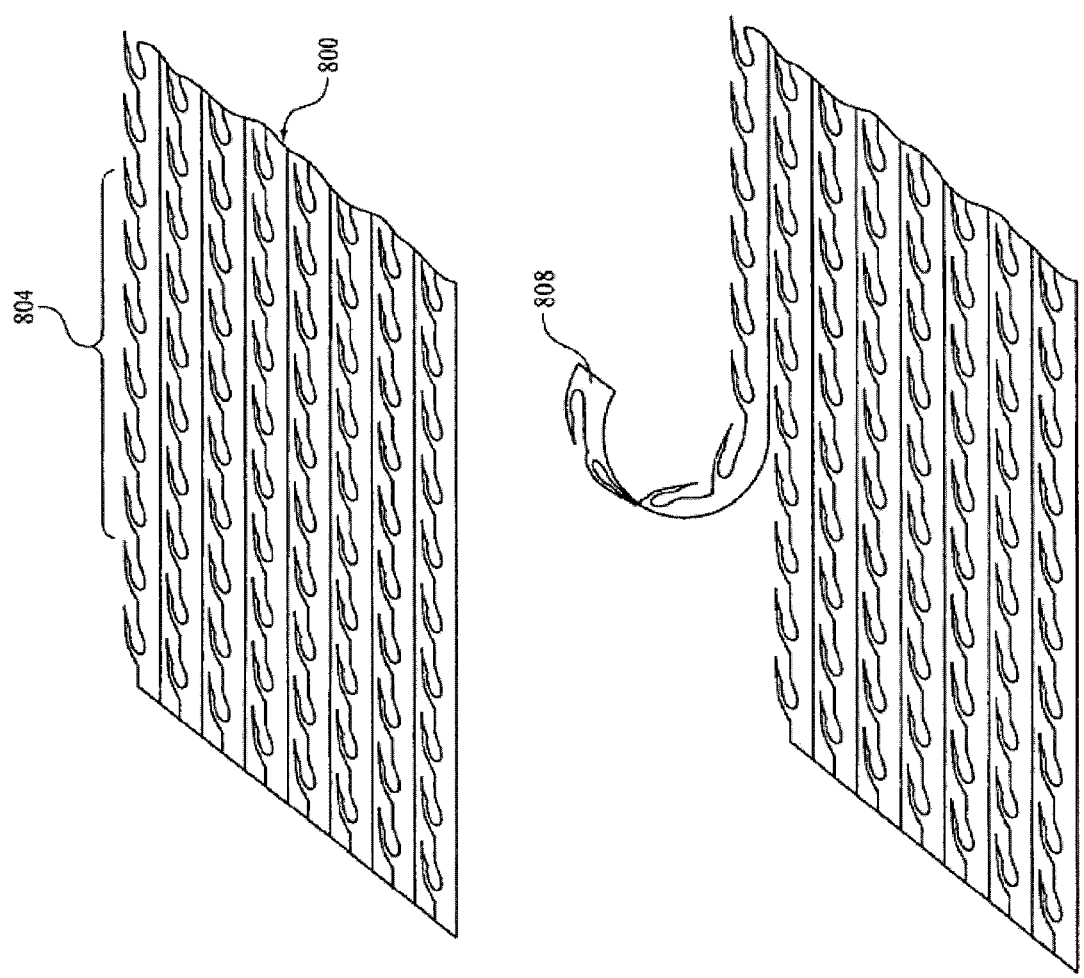
FIG. 18 shows a step in a method of fabricating the electrodes of the present invention.

As indicated above, the body of the electrodes of the present invention may be fabricated as a single integrated unit made of one conductive material. In other embodiments, the electrodes are constructed of multiple components with such configurations providing a simple manner for the large-scale manufacture of the electrodes. A side-view of the multi-component embodiment of the electrode 700 shown in FIG. 17 contains an electrode rim 704 that includes the electrode teeth as described hereinabove and a constraining wall 708 which makes up the remainder of the electrode body. Both the constraining wall 708 and the electrode rim 704 that includes the electrode teeth may be cylinders. The constraining wall 708 may have an alignment notch 712 along its exterior face. The depth of the alignment notch 712 may be set so that the maximum penetrating depth of the electrode teeth is set to depth D 716 as shown. The constraining wall 708 may be fabricated from either metal or plastic as described further hereinbelow. In this configuration the rim of the electrode that includes the electrode teeth 704 fits tightly over the constraining wall 708 such that the two form an integrated electrode body 700. The electrodes may be formed as concentric circles As described above for the blunt bullet-shaped electrode, cylindrical electrodes may also be fabricated using a similar technique. The electrode rim that includes the electrode teeth 704 may be fabricated using the commonly known technique of photochemical etching (or photochemical milling). The repeating pattern of teeth 804 (as also shown in FIG. 2) may be printed as an etchant-resistant chemical onto both sides of a sheet of metal 800, e.g. stainless steel. The pattern 804 may have the design of the opened electrode cylinder. The pattern 804 could be repeated multiple times on the same sheet of metal 800, such as shown in FIG. 18A. After the etchant-resistant chemical dries, the metal is exposed to the etching reagent and those portions which are not protected by the etchant-resistant chemical are eroded. After such erosion, the remaining metallic strip 808 is in the shape of the proximal rim of the open electrode cylinder including the electrode teeth. The metallic strip 808 may then be closed and fused using well-known techniques, such as tack welding, to form the cylindrical electrode body. The metallic strip 808 may be formed into a cylinder around the constraining wall (FIG. 7) to ensure a tight fit between the two components and so that the depth of the electrode teeth may be set appropriately.

In other embodiments, the constraining wall may be formed from a plastic mold. In those embodiments, the metallic strip may include holes in the body of the strip where plastic could flow during molding, thereby forming a strong connection between the two components once the plastic dries. One of skill in the art will recognize variations of these methods for the fabrication of the electrodes of the present invention, such as negative etching or standard high-precision machining.

Although the electrodes of the present invention may be applied manually, in cases where a large number of electrodes need to be installed, the electrode technician might hand-pick individual electrodes from a container which takes a significant amount of time. In addition, it is often desirable to know the exact coordinates of the electrodes on the patient's body (e.g., scalp) relative to a known reference point. Although these coordinates can be acquired using a Polhemus sensor, such processes are time consuming for the administration of a large number of electrodes. In order to address these issues, the present invention may also include a "volley gun"-like electrode installation device. Since the electrodes of the present invention need not have leads attached prior to installation, a pack of electrodes of identical size may be loaded into the electrode installation device, greatly reducing the time between electrode installations. The electrode installation device may also be equipped with a coordinate sensor, e.g., similar to a Polhemus sensor, to record the coordinates of each electrode as it is installed on the patient's skin, taking little extra time during operation.

Figure 19:
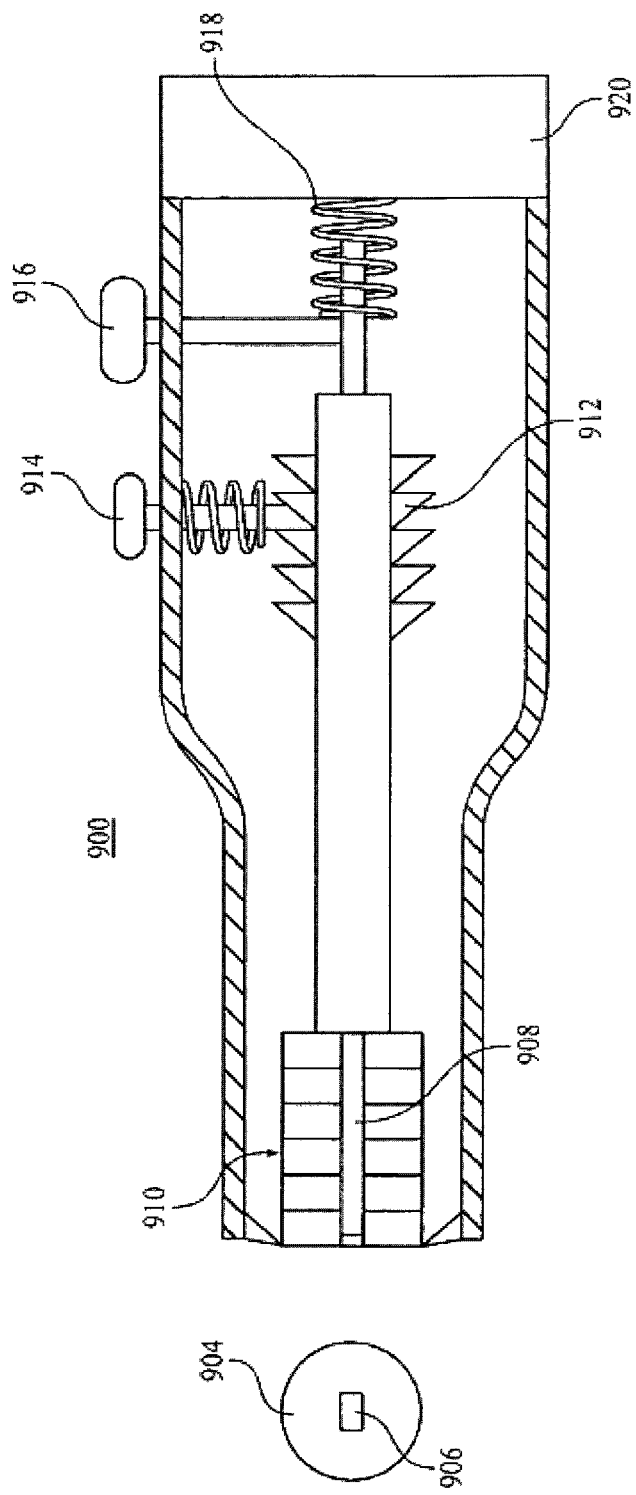
FIG. 19 displays a schematic of an electrode installation device of the present invention.

An example of the electrode installation device 900 is shown in FIG. 19. In this embodiment, the electrode 904 has a non-circular (e.g., square or hexagonal) central hole 906 that allows the electrode to be twisted by a rod 908. A pack of electrodes 910 is stepped forward by a stepping assembly which may contain a gear 912, and buttons 914 and 916. A spring 918 may be utilized to load the next electrode automatically. A position sensor 920, which may contain a radio frequency (RF) circuit, measures electrode location and transmits the result (either wirelessly or via a wire) to a computer after each electrode installation.

The electrodes of the present invention may be used for various physiological recording techniques such as traditional EEG, EKG, EMG, and other electrophysiological applications. The present invention may also be used in other applications where the device is not used as an electrode. Because of the strength with which the electrodes may be attached to the skin, they may be used to anchor another device onto the skin more securely than by employing standard adhesive tape. For example, when equipped with the appropriate electronic components, the electrodes of the present invention may be used to assess a variety of additional physiological measures such as blood oxygenation and blood glucose levels. With a leak-preventive seal, a liquid-form drug may be stored within the chamber of the device and delivered transcutaneously. Drug delivery may also benefit from electrically induced and controlled electroporation in which a transcutaneous current is utilized to open microscopic channels through which drug may be delivered through the skin in a desired amount.

The electrodes of the present invention may also be used to stimulate muscle tissue. Microcurrent stimulation of muscles may be employed to treat age-related macular degeneration, wound healing, tendon repair, and ruptured ligament recovery. Further, the present invention may be used to stimulate muscle to improve their strength such as in patients suffering from osteoarthritis or to preserve muscle tone and mass during extended periods of disuse such as coma or surgery recovery. Electric simulation of muscles may also be utilized to mimic the effect of exercise in weight management.

The electrodes of the present invention may be connected to a variety of electronic components to enable a diversity of technical and medical implementations. Examples include: 1) a game system controlled by the EEG patterns of the player, where those EEG signals are measured using electrodes of the present invention; 2) a robotic system that serves a paralyzed patient by employing measurements of patients' EEG and EMG signals assessed through the electrodes of the present invention; 3) an ambulatory EEG recorder employing electrodes of the present invention for emergency medical care; 4) an automatic drowsiness monitor for motor vehicle drivers; and 5) a diagnostic tool for animals in a veterinary setting. The wireless design of the present invention greatly facilitates a number of specialized experimental applications, such as unconstrained neurophysiological monitoring during behavior, where it is preferred for animal or human subjects to have free range of motion within an environment.

Those of skill in the art will recognize that numerous modifications of the above-described process can be performed without departing from the present invention. For example, modification of the specific geometry and spacing of the teeth of the electrodes and variation of the electronic components coupled to the present invention are considered to be within the scope of the present invention.

The invention claimed is:

1. An electrode system for attaching an electrode to skin of a patient, comprising: an electrode having an electrode body comprising an electrode face that is adapted to be pressed against the skin of the patient, wherein said electrode face includes a plurality of teeth that includes teeth located on a rim at a perimeter of said electrode body, wherein each of said plurality of teeth includes a shaft that initially extends from said electrode face, the shaft then turning to run at an orientation that is within about 5° away from the rim to a depth that is less than a depth of stratum corneum of said patient.

2. The electrode system of claim 1, further comprising a cap that is connected to a distal portion of said electrode body.

3. The electrode system of claim 1, wherein said plurality of teeth includes teeth located across the electrode face.

4. The electrode system of claim 1, wherein the electrode body is a hollow cylinder.

5. The electrode system of claim 1, wherein said electrode body is a cylinder, a blunt bullet, or a disk.

6. The electrode system of claim 2, wherein said cap comprises a magnetic material and is shaped as a cylindrical disk having a hole.

7. The electrode system of claim 6, further comprising a spherical magnetic lead that is adapted to fit snugly into the hole.

8. The electrode system of claim 7, wherein at least one of said teeth, said cap, and said spherical magnetic lead is coated or electroplated with a conductive material.

9. The electrode system of claim 8, further comprising a rubber ring that covers said electrode teeth when said electrode is not attached to said patient.

10. A method of fabricating an electrode comprising the steps of:
applying an etchant-resistant chemical to the surface of a sheet of material in a pattern, said pattern including a plurality of teeth on a rim of said pattern, wherein each of said plurality of teeth includes a shaft that initially extends from said rim and then turns to run at an orientation that is within about 5° away from the rim to a depth that is less than a depth of stratum corneum of a patient;
etching said sheet of material with an etchant solution;
forming said electrode from said non-etched material, wherein said electrode has an electrode face that is adapted to be pressed against the skin of the patient, wherein said electrode face includes said plurality of teeth.

11. The method of claim 10, wherein said forming step includes rolling said sheet of material into a cylinder.

12. The method of claim 11, further comprising a step of fusing said sheet into said cylinder after said forming step.

13. The method of claim 12, wherein said fusing is achieved using adhesive, soldering, epoxy, or sintering.

14. The method of claim 10, further comprising a step of coating said sheet of material with a layer of sintering agent prior to said etching step.

15. The method of claim 10, wherein said fusing is achieved using sintering, and further comprising a step of heat-treating said electrode to achieve said sintering after said forming step.

16. The method of claim 11, wherein said cylinder defines a body of said electrode.

17. The method of claim 10, wherein said forming step comprises rolling said sheet of material into a coil to form a body of said electrode having an electrode face.

18. The method of claim 17, wherein said plurality of said teeth is located on said electrode face.

19. The method of claim 18, wherein said body of said electrode is a cylinder, a blunt bullet, or a disk.

20. The method of claim 17, further comprising a step of fusing said sheet into said coil after said forming step.

21. The method of claim 20, wherein said fusing is achieved using adhesive, soldering, epoxy, or sintering.

22. The method of claim 21, further comprising a step of coating said sheet of material with a layer of sintering agent prior to said etching step.

23. The method of claim 21, wherein said fusing is achieved using sintering, and further comprising a step of heat-treating said electrode to achieve said sintering after said forming step.

24. An electrode for attachment to skin of a patient, comprising:
an electrode body having a proximal surface and a distal surface;
a plurality of teeth situated at the proximal surface of the electrode body, the plurality of teeth including teeth situated on a rim at a perimeter of the electrode body, wherein each of said plurality of teeth is situated at a corresponding indentation of the proximal surface of the electrode body, and is defined by a proximal tooth surface that extends from the proximal surface of the electrode body at the associated indentation along an arc having a terminal portion that is at an orientation that is within about 5° away from the proximal surface of the electrode body, and is further defined by a distal tooth surface that extends opposite the proximal tooth surface from the electrode body at the associated indentation to the terminal portion of the proximal tooth surface so that the proximal tooth surface and the distal tooth surface form a sharp end.

25. The electrode of claim 24, wherein the terminal portions of the proximal tooth surfaces of each of the plurality of teeth are oriented at an angle of between 4 degrees and 5 degrees from an unindented portion of the proximal surface of the electrode body.

26. The electrode of claim 24, wherein the electrode body is cylindrical, and the proximal surface of the electrode body is a circular annulus.

27. The electrode of claim 26, wherein the sharp ends of the plurality of teeth are aligned such that adjacent teeth are oriented in a substantially common direction.

28. The electrode system of claim 1, wherein the electrode body is bullet-shaped about a central axis and the teeth of the plurality of teeth are distributed on a bullet-shaped surface along the central axis, wherein the sharp ends of the plurality of teeth are aligned so as to face tangentially along the tooth proximal surfaces in directions perpendicular to the central axis so that adjacent teeth are oriented in a substantially common direction.

29. A method of fabricating an electrode comprising the steps of:
applying an etchant-resistant chemical to the surface of a sheet of material in a pattern, the pattern defining a plurality of teeth situated at a proximal surface of an electrode body of the electrode, the plurality of teeth including teeth situated on a rim at a perimeter of the electrode body, each of said plurality of teeth is situated at a corresponding indentation of the proximal surface of the electrode body, and is defined by a proximal tooth surface that extends from the proximal surface of the electrode body at the associated indentation along an arc having a terminal portion that is at an orientation that is within about 5° away from the proximal surface of the electrode body, and a distal tooth surface that extends opposite the proximal tooth surface from the electrode body at the associated indentation to the terminal portion of the proximal tooth surface, so that the proximal tooth surface and the distal tooth surface form a sharp end; etching said sheet of material with an etchant solution; and forming said electrode from said non-etched material, wherein said electrode has an electrode face that is adapted to be pressed against the skin of the patient, wherein said electrode face includes said plurality of teeth.

* * * * *

UNITED STATES PATENT AND TRADEMARK OFFICE
CERTIFICATE OF CORRECTION

PATENT NO. : 9,504,424 B2  
APPLICATION NO. : 14/359904  
DATED : November 29, 2016  
INVENTOR(S) : Jia et al.

Page 1 of 1

It is certified that error appears in the above-identified patent and that said Letters Patent is hereby corrected as shown below:

In the Specification

Column 1, beginning at Line 14, please insert:
--STATEMENT OF GOVERNMENT SUPPORT
This invention was made with government support under grant number NS036888, awarded by the National Institutes of Health. The government has certain rights in the invention.--

Signed and Sealed this  
Twenty-fourth Day of September, 2019

Andrei Iancu  
*Director of the United States Patent and Trademark Office*